United States Patent
Chen et al.

(10) Patent No.: US 8,530,674 B2
(45) Date of Patent: Sep. 10, 2013

(54) PROCESS FOR PREPARING (S)-(+)-N-METHYL-3-(1-NAPHTHYLOXY)-3-(2-THIENYL) PROPYLAMINE BY USING OPTICALLY ACTIVE METHYLHYDROXYLAMINOPROPANOL COMPOUND AS INTERMEDIATE

(75) Inventors: Bo-Fong Chen, Taichung (TW); Feng-Ju Lu, Taoyuan (TW); Jinun-Ban Yeh, Hsinchu (TW); Wei-chyun Wong, Taipei (TW)

(73) Assignee: SCI Pharmtech, Inc. (TW)

( * ) Notice: Subject to any disclaimer, the term of this patent is extended or adjusted under 35 U.S.C. 154(b) by 392 days.

(21) Appl. No.: 12/774,933

(22) Filed: May 6, 2010

(65) Prior Publication Data

US 2011/0275835 A1    Nov. 10, 2011

(51) Int. Cl.
*A61K 31/38* (2006.01)
*C07D 333/22* (2006.01)

(52) U.S. Cl.
USPC ............................................ 549/72; 514/438

(58) Field of Classification Search
None
See application file for complete search history.

(56) References Cited

U.S. PATENT DOCUMENTS 7,538,232 B2 * 5/2009 Butchko et al. ................. 549/75
7,829,731 B2 * 11/2010 Chen et al. ...................... 549/75

FOREIGN PATENT DOCUMENTS

WO    WO 2007062119 A1 * 5/2007

OTHER PUBLICATIONS

Wang, G. et al Tetrahedron Asymmetry 2005 vol. 16 pp. 1873-1879.*

* cited by examiner

*Primary Examiner* — Janet Andres
*Assistant Examiner* — Heidi Reese
(74) *Attorney, Agent, or Firm* — Berliner & Associates

(57) ABSTRACT

The present invention provides (S)-methylhydroxylaminopropanol compound as an intermediate in preparation of (S)-(+)-N-methyl-3-(1-naphthyloxy)-3-(2-thienyl)propylamine. The present invention also provides a process for preparing (S)-(+)-N-methyl-3-(1-naphthyloxy)-3-(2-thienyl)propylamine with higher yield and lower cost by using the (S)-methylhydroxylaminopropanol compound as an intermediate.

12 Claims, No Drawings

PROCESS FOR PREPARING (S)-(+)-N-METHYL-3-(1-NAPHTHYLOXY)-3-(2-THIENYL)PROPYLAMINE BY USING OPTICALLY ACTIVE METHYLHYDROXYLAMINOPROPANOL COMPOUND AS INTERMEDIATE

BACKGROUND OF THE INVENTION

1. Field of the Invention

The present invention relates to a process for preparing (S)-(+)-N-methyl-3-(1-naphthyloxy)-3-(2-thienyl)propylamine and its pharmaceutically acceptable salts with high enantiomeric excess (ee) and high chemical purity by using chiral compounds as an intermediate.

2. Description of Related Art (S)-(+)-N-methyl-3-(1-naphthyloxy)-3-(2-thienyl)propylamine (Duloxetine®) hydrochloride salt is used as an antidepressant for medical therapy. There are various processes for preparing Duloxetine®. For example, U.S. Pat. No. 7,538,232 discloses a process for preparation of Duloxetine® by reacting (S)-3-methylamino-1-(2-thienyl)propan-1-ol and 1-fluoronaphthalene with potassium hydroxide in a mixed solvent system (i.e., DMSO and toluene) in order to preserve chiral integrity. However, due to different types of organic solvents used in the process for the preparation of Duloxetine®, cost of subsequent treatment increases. In addition, the usage of mixed organic solvents is disadvantageous to environmental protection. Therefore, there is still a need to provide a process for preparing chiral Duloxetine®.

SUMMARY OF THE INVENTION

The present invention provides a simple and safe process for preparing Duloxetine® with high purity and quality. Particularly, the present invention provides a compound of formula (II)

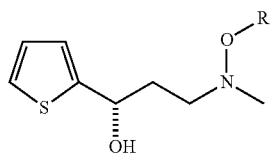

(II)

wherein R is a hydrogen atom, $C_{1-8}$ alkyl or $C_{1-6}$ aryl, and the absolute configuration of a chiral center thereof is S.

In one aspect, the present invention provides use of the compound of formula (II) as an intermediate in preparation of (S)-(+)-N-methyl-3-(1-naphthyloxy)-3-(2-thienyl)propylamine (Duloxetine®).

In another aspect, the present invention provides a process for preparing (S)-(+)-N-methyl-3-(1-naphthyloxy)-3-(2-thienyl)propyl amine (Duloxetine®) with higher yield and lower cost by using (S)-3-methylamino-1-(2-thienyl)-propan-1-ol, which has a structure of formula (III) and is produced from the intermediate of formula (II).

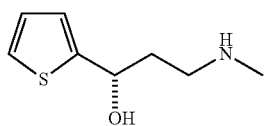

III (S)-3-methylamino-1-(2-thienyl)propan-1-ol

In the present invention, the process for preparing Duloxetine® is summarized in the following scheme 1 and includes steps of: (1) performing a Mannich reaction of 2-acetylthiophene, formaldehyde and a compound represented by formula HNCH$_3$(OR) to form a compound represented by formula (I); (ii) enatioselectively reducing the compound represented by formula (I) to a compound represented by formula (II); (iii) performing an N,O-cleavage reaction on the compound represented by formula (II) to give (S)-(−)-3-methylamino-1-(2-thienyl)-propan-1-ol as shown by formula (III); and (iv) reacting the (S)-(−)-3-methylamino-1-(2-thienyl)-propan-1-ol with halonaphthalene to form (S)-(+)-N-methyl-3-(1-naphthyloxy)-3-(2-thienyl)propylamine (Duloxetine®), wherein R is a hydrogen atom, $C_{1-8}$ alkyl or $C_{6-10}$ aryl, preferably $C_{1-4}$ alkyl, and more preferably methyl; and halo is F, Cl, Br or I.

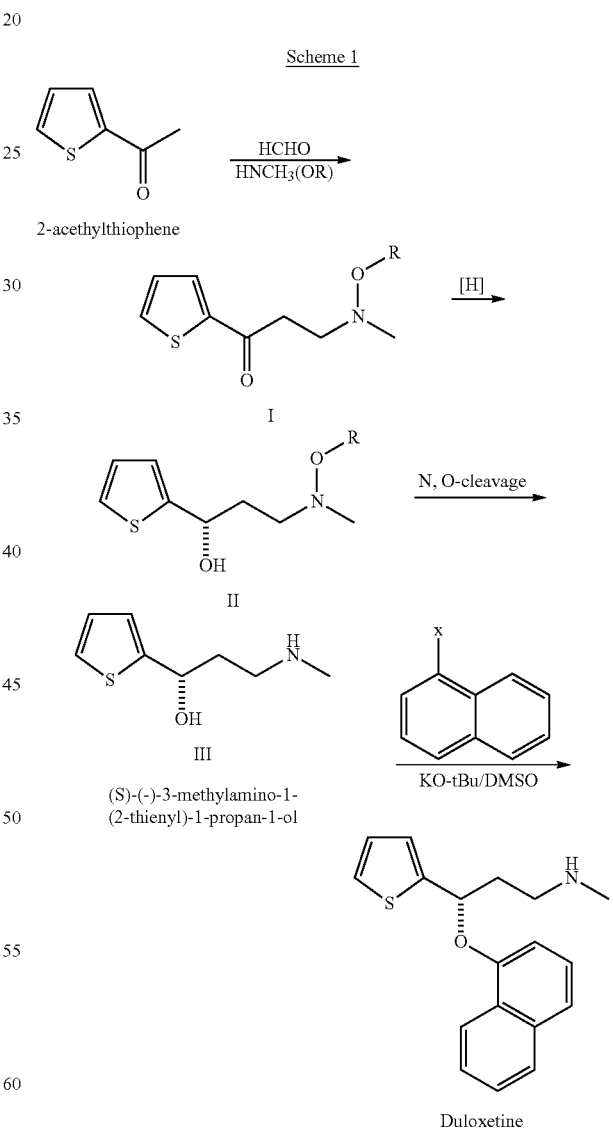

Scheme 1

Further, in the step (iv) of the process of the present invention, KOR$_1$ and DMSO are used in the naphthalenation reaction, wherein R$_1$ is $C_{1-6}$ alkyl, preferably butyl, and more preferably tert-butyl.

DETAILED DESCRIPTION OF PREFERRED EMBODIMENTS

The following illustrative embodiments are provided to illustrate the disclosure of the present invention. These and other advantages and effects can be apparently understood by those in the art after reading the disclosure of this specification.

The present invention provides a compound represented by formula (II) in optical active form:

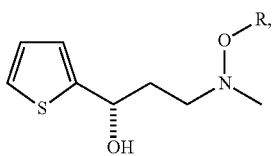

wherein R is a hydrogen atom, $C_{1-8}$ alkyl or $C_{6-10}$ aryl, preferably $C_{1-4}$ alkyl, and more preferably methyl. Furthermore, an absolute configuration of a chiral center of the compound is S.

Furthermore, the present invention provides a process for preparing (S)-(+)-N-methyl-3-(1-naphthyloxy)-3-(2-thienyl) propylamine (Duloxetine®), wherein the compound represented by formula (II) is used as an intermediate. The process of the present invention is summarized in Scheme 1.

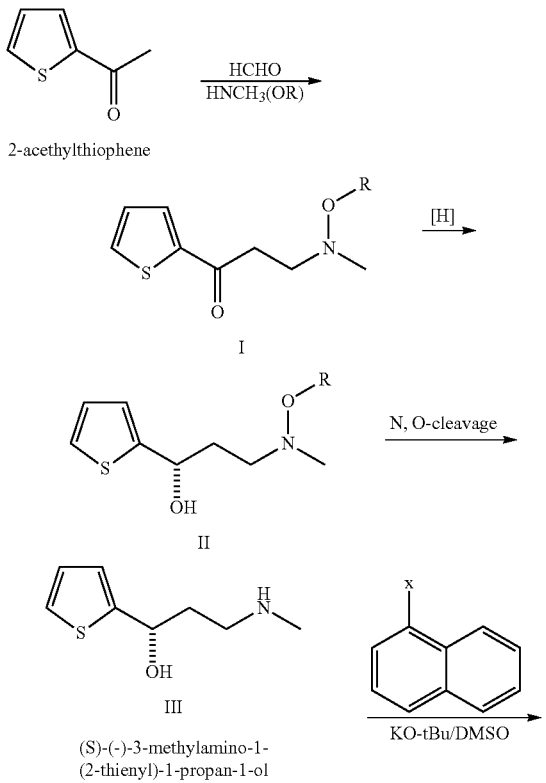

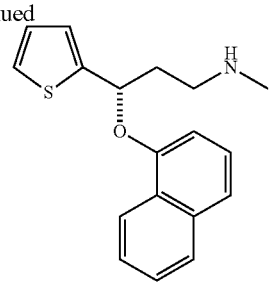

Duloxetine

In the above Scheme 1, R is a hydrogen atom, $C_{1-8}$ alkyl or $C_{6-10}$ aryl, preferably $C_{1-4}$ alkyl, and more preferably methyl; halo is F, Cl, Br or I; and $R_1$ is $C_{1-6}$ alkyl, preferably butyl, and more preferably tert-butyl.

In more details, the process of the present invention includes steps of:
(i) performing a Mannich reaction of 2-acetylthiophene, formaldehyde and a compound represented by formula $HNCH_3(OR)$ to form a compound represented by formula (I);
(ii) enatioselectively reducing the compound represented by formula (I) to a compound represented by formula (II);
(iii) performing an N,O-cleavage reaction on the compound of formula (II) to form (S)-(−)-3-methylamino-1-(2-thienyl)-propan-1-ol as shown by formula (III); and
(iv) reacting the (S)-(−)-3-methylamino-1-(2-thienyl)propan-1-ol with halonaphthalene to form (S)-(+)-N-methyl-3-(1-naphthyloxy)-3-(2-thienyl) propylamine (Duloxetine®).

The step (i) of the process is carried out at a temperature ranged from 15° C. to 90° C., preferably from 40° C. to 80° C., and more preferably from 50° C. to 70° C. The compound of formula (I) obtained in the step (i) is either as a free form or as an acid addition salt.

The reduction of the compound represented by formula (I) in the step (ii) is asymmetric reduction, and preferably chiral reduction. Hence, an optically active form of the compound represented by formula (II) is obtained. The optically active form can be obtained via asymmetric hydrogenation using a catalyst with chiral ligands, or a hydride with chiral ligands. In the step (ii), a chiral reducing agent used in the chiral reduction is selected from the group consisting of complex hydride, borane, transition metal catalyst and microbial dehydrogenase.

In one preferred embodiment, the reduction of the compound of formula (I) in the step (ii) is carried out in a mixture of an alcohol (such as methanol) and a base (such as potassium tert-butoxide), and in the presence of a catalyst that includes an enantiomer-enriched bidentate phosphorus-containing ligand, a transition metal and a diamine, preferably a chiral diamine. An example of the catalyst is $RuCl_2((R)\text{-}3,5\text{-xylyBINAP})((2R)\text{-DAIPEN})$. The reaction mixture is hydrogenated at predetermined pressure to yield the compound of formula (II) with a high ee value.

In the step (iii) of the process of the present invention, the N,O-cleavage reaction of the compound represented by formula (II) is carried out by hydrogenation in the presence of a catalyst such as Raney-nickel, or by chemical reduction processes such as those by using $LiAlH_4$ or zinc metal as a reducing agent.

In the step (iv) of the process of the present invention, the reaction of (S)-(−)-3-methylamino-1-(2-thienyl)propan-1-ol and halonaphthalene is carried out by using a proper base such as potassium tert-butoxide in a suitable amount of DMSO to form (S)-(+)-N-methyl-3-(1-naphthyloxy)-3-(2-thienyl)propylamine (Duloxetine®). The excess amount of halonaphthalene, ranging from about 1.5 to 4 equivalents, can be recovered. The reaction is performed at a temperature ranged from 20° C. to 110° C., preferably from 40° C. to 90° C., for 1 to 24 hours. One embodiment of the present invention is conducted in the presence of excess halonaphthalene and a suitable amount of DMSO to overcome the problems regarding racemization and environmental protection. In one preferred embodiment, DMSO is used in amounts ranging from one to ten times the amount of (S)-(−)-3-methylamino-1-(2-thienyl)propan-1-ol, more preferably from one to five times the amount of (S)-(+3-methylamino-1-(2-thienyl)propan-1-ol.

In comparison with the prior art, the process of the present invention provides optically pure Duloxetine® with higher yield and lower cost. This process should operate particularly well on an industrial scale regarding to economic and ecological aspects.

EXAMPLES

Example 1

Synthesis of
3-methoxymethylamino-1-(2-thienyl)-1-propanone
hydrochloride salt

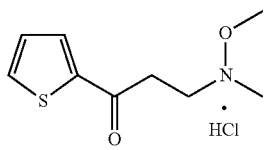

27.7 g of N,O-dimethylhydroxylamine hydrochloride, 9.3 g of paraformaldehyde, 6.4 g of hydrochloride (32%), 30.0 g of 2-acetylthiophene and 100 g of isopropanol were provided into a flask. After being stirred at 60° C. for 13 hours, the reaction mixture was cooled down to room temperature. The crystal thus formed was filtered, washed with 30 g of isopropanol and dried under reduced pressure to obtain 42.5 g of 3-methoxymethylamino-1-(2-thienyl)-1-propanone hydrochloride salt (75.9%).

$^1$H NMR (400 MHz, CDCl$_3$) δ (ppm)=3.1 (s, 3H), 3.7-3.8 (br, 4H), 4.1 (s, 3H), 7.2 (t, J=4.5 Hz, 1H), 7.7 (d, J=4.9 Hz, 1H), 7.9 (d, J=3.5 Hz, 1H).

Example 2

Synthesis of (S)-3-methoxymethylamino-1-(2-thienyl)propan-1-ol

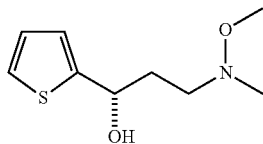

A degassed methanol solution (4 mL) containing RuCl$_2$((R)-3,5-xylylBINAP)((2R)-DAIPEN) (10 mg), 3-methoxymethylamino-1-(2-thienyl)-1-propanone (160 mg), potassium tert-butoxide (100 mg) and methanol (10 mL) was charged in a glass autoclave under an argon gas flow. After deaeration and replacement by argon, hydrogen was introduced to a predetermined pressure. The resulting solution was hydrogenated at 20° C. for 12 hours. Upon completion of hydrogenation, the reaction mixture was concentrated to give an oily product (161 mg, 95.8% measured by HPLC assay, 95% ee).

$^1$H NMR (400 MHz, CDCl$_3$) δ (ppm)=3.0 (s, 3H), 3.0-3.1 (m, 1H), 4.1 (s, 3H), 4.0-4.1 (m, 3H), 6.1 (dt, J=7.4, 15.4 Hz, 1H), 6.9 (d, J=15.7 Hz, 1H), 7.0 (dd, J=3.7, 5.0 Hz, 1H), 7.1 (d, J=3.4 Hz, 1H).

Example 3

Synthesis of (S)-(−)-3-methylamino-1-(2-thienyl)-propan-1-ol

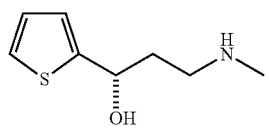

(S)-3-methoxymethylamino-1-(2-thienyl)propan-1-ol obtained from Example 2 was dissolved in 10 ml of methanol with 8 mg of Raney-nickel. This resulting solution was provided in a glass autoclave and hydrogenated at 50° C. for 12 hours. Upon completion of hydrogenation, the reaction mixture was filtered, and the solvent was removed under reduced pressure to give a crystal compound (122 mg, 90.8% measured by HPLC assay, 95% ee). The crude product was further purified by re-crystallization in toluene to give a product with optical purity as high as 100% ee.

Example 4

Synthesis of (S)-(+)-N-methyl-3-(1-naphthyloxy)-3-(2-thienyl)propylamine (Duloxetine®)

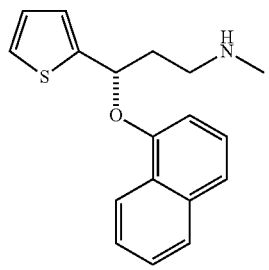 [SMILES: CNCC[C@H](Oc1cccc2ccccc12)c1cccs1]

(S)-(−)-3-methylamino-1-(2-thienyl)-propan-1-ol (20.0 g) and 1-fluoronaphthalene (68.3 g) were charged into a 4-neck round bottomed flask. Potassium tert-butoxide (13.1 g) and DMSO (36.0 g) were then added, and the resulting mixture was heated to 60° C. for 8 hours. After completion of the reaction, the reaction mixture was cooled down and washed with water. Layers were separated, and the organic layer was further extracted with 32% HCl$_{(aq)}$ (14.7 g) to separate Duloxetine® from 1-floronaphthalene. The acidic aqueous layer was adjusted to pH 12-13 with 45% NaOH$_{(aq)}$ (17.6 g) to obtain Duloxetine® in a free base form as an oily liquid (31.3 g, 90%). Optical purity of the resulting Duloxetine® measured by chiral HPLC was 95% e.e.

$^1$H NMR (400 MHz, CDCl$_3$) δ (ppm)=2.2 (m, 1H), 2.4 (m, 1H), 2.4 (s, 3H), 2.8 (m, 2H), 5.8 (m, 1H), 6.8 (d, 1H), 6.9 (m, 1H), 7.1 (d, 1H), 7.2 (d, 1H), 7.3 (d, 1H), 7.4 (m, 1H), 7.5 (m, 2H), 7.8 (m, 1H), 8.3 (m, 1H).

The foregoing descriptions of the detailed embodiments are only illustrated to disclose the features and functions of the present invention and not restrictive of the scope of the present invention. Accordingly, the protection sought herein is as set forth in the claims below.

What is claimed is:

1. A process for preparing (S)-(+)-N-methyl-3-(1-naphthyloxy)-3-(2-thienyl)propylamine, comprising steps of:
    performing an N,O-cleavage reaction on a compound represented by formula (II),

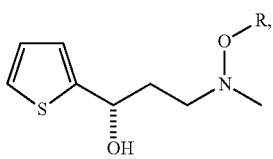

(II)

to form (S)-(−)-3-methylamino-1-(2-thienyl)propan-1-ol as shown in formula (III),

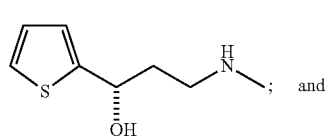

(III)

and reacting the (S)-(−)-3-methylamino-1-(2-thienyl)propan-1-ol with halonaphthalene in DMSO to form (S)-(+)-N-methyl-3-(1-naphthyloxy)-3-(2-thienyl)propylamine represented by the following formula,

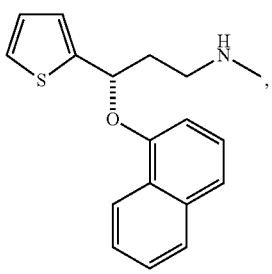

wherein R is a hydrogen atom, C$_{1-8}$ alkyl or C$_{6-10}$ aryl; and halo is F, Cl, Br or I, wherein KOR$_1$ is used in the step of reacting the (S)-(−)-3-methylamino-1-(2-thienyl)propan-1-ol with halonaphthalene, and wherein R$_1$ is C$_{1-6}$ alkyl.

2. The process of claim 1, wherein R is C$_{1-4}$ alkyl.

3. The process of claim 2, wherein R is methyl.

4. The process of claim 1, wherein the halonaphthalene is 1-fluoronaphthalene.

5. The process of claim 1, wherein R$_1$ is tert-butyl.

6. The process of claim 1, wherein the reaction of the (S)-(−)-3-methylamino-1-(2-thienyl)propan-1-ol with halonaphthalene is carried out in presence of excess halonaphthalene, and wherein DMSO is used in amounts ranging from one to ten times the amount of (S)-(−)-3-methylamino-1-(2-thienyl)propan-1-ol.

7. The process of claim 6, wherein DMSO is used in amounts ranging from one to five times the amount of (S)-(−)-3-methylamino-1-(2-thienyl)propan-1-ol.

8. A process for preparing (S)-(+)-N-methyl-3-(1-naphthyloxy)-3-(2-thienyl)propylamine represented by the following formula,

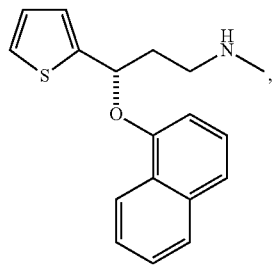 [SMILES: CNCC[C@H](Oc1cccc2ccccc12)c1cccs1]

comprising reacting (S)-(−)-O-3-methylamino-1-(2-thienyl)propan-1-ol with KOR$_1$ and halonaphthalene in DMSO, wherein R$_1$ is C$_{1-6}$ alkyl; and halo is F, Cl, Br or I.

9. The process of claim 8, wherein R$_1$ is tert-butyl.

10. The process of claim 8, wherein the halonaphthalene is 1-fluoronaphthalene.

11. The process of claim 8, wherein the reaction of the (S)-(−)-O-3-methylamino-1-(2-thienyl)propan-1-ol (III) with KOR$_1$ and halonaphthalene in DMSO is carried out in presence of excess halonaphthalene, and wherein DMSO is used in amounts ranging from one to ten times the amount of (S)-(−)-3-methylamino-1-(2-thienyl)propan-1-ol.

12. The process of claim 11, wherein DMSO is used in amounts ranging from one to five times the amount of (S)-(−)-3-methylamino-1-(2-thienyl)propan-1-ol.

* * * * *